US012700501B2

(12) United States Patent
Redder et al.

(10) Patent No.: US 12,700,501 B2
(45) Date of Patent: Aug. 4, 2026

(54) MULTI-TECHNOLOGY WIRELESS COMMUNICATION NETWORK NETWORK FOR MONITORING PATIENT THROUGH-OUT A HEALTHCARE FACILITY

(71) Applicant: KONINKLIJKE PHILIPS N.V., Eindhoven (NL)

(72) Inventors: Paul Franz Redder, Newberry, FL (US); Bruce Geoffrey Appleton, Orlando, FL (US); Jose H. Chacon, Pembroke Pines, FL (US); Aman Singh, Orlando, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 129 days.

(21) Appl. No.: 18/694,684

(22) PCT Filed: Sep. 20, 2022

(86) PCT No.: PCT/EP2022/076017
§ 371 (c)(1),
(2) Date: Mar. 22, 2024

(87) PCT Pub. No.: WO2023/046652
PCT Pub. Date: Mar. 30, 2023

(65) Prior Publication Data
US 2024/0404691 A1      Dec. 5, 2024

Related U.S. Application Data

(60) Provisional application No. 63/247,420, filed on Sep. 23, 2021.

(51) Int. Cl.
*G16H 40/40* (2018.01)
*G16H 10/60* (2018.01)
(Continued)

(52) U.S. Cl.
CPC ............. *G16H 40/40* (2018.01); *G16H 10/60* (2018.01); *H04W 76/15* (2018.02); *H04W 64/003* (2013.01)

(58) Field of Classification Search
CPC ....... G16H 40/40; G16H 10/60; H04W 76/15; H04W 64/003; G01R 33/288; G01R 33/28
See application file for complete search history.

(56) References Cited

U.S. PATENT DOCUMENTS

2002/0013518 A1    1/2002  West
2002/0084698 A1*   7/2002  Kelly ................... A61B 5/0006
                                                      361/728
(Continued)

OTHER PUBLICATIONS

International Search Report Dated Jan. 3, 2023 for International Appln No. PCT/EP2022/076017 Filed Sep. 20, 2022.
(Continued)

*Primary Examiner* — Ryan W Sherwin

(57) ABSTRACT

A method (400) for providing continuous wireless connectivity for monitoring a patient throughout a healthcare facility, including: providing (402) an in-room access point in a room defined at least in part by shielding walls and an access point outside the room and connecting the in-room access point and the access point; (ii) transmitting (404), by a communication unit of a first source device, information related to the patient; (iii) receiving (406), by the access point outside the room, information from the first source device; (iv) receiving (408), by the in-room access point, additional information from the first source device; (v) combining (410), the information and the additional information from the first source device to generate a digital data stream; and (vi) transmitting (412), by an access point
(Continued)

communication unit of the access point system, the digital data stream to an information system of the healthcare facility.

15 Claims, 6 Drawing Sheets

(51) Int. Cl.
  *H04W 76/15*    (2018.01)
  *H04W 64/00*    (2009.01)

(56)                  References Cited

U.S. PATENT DOCUMENTS

| | | | |
|---|---|---|---|
| 2005/0107681 A1 | 5/2005 | Griffiths | |
| 2006/0094936 A1* | 5/2006 | Russ | G16H 40/67 |
| | | | 600/300 |
| 2006/0241384 A1 | 10/2006 | Fisher | |
| 2009/0112630 A1* | 4/2009 | Collins, Jr. | H04L 67/125 |
| | | | 705/2 |
| 2012/0215092 A1 | 8/2012 | Harris | |
| 2014/0275970 A1 | 9/2014 | Brown | |
| 2019/0046034 A1 | 2/2019 | Hawkes | |
| 2019/0183705 A1* | 6/2019 | Bodurka | H04B 5/48 |
| 2019/0377042 A1* | 12/2019 | Anderson | G01R 33/3692 |
| 2020/0288332 A1* | 9/2020 | Annambhotla | H04L 67/34 |
| 2023/0068520 A1* | 3/2023 | Sukkau | G01R 33/28 |

OTHER PUBLICATIONS

Kim Yena et al: "Energy-efficient wireJ.ess hospitaJ. sensor networking for remote patient monitoring", Information Sciences, Elsevier, Amsterdam, NL, vol. 282, Jun. 10, 2014 (Jun. 10, 2014), pp. 332-349.

* cited by examiner

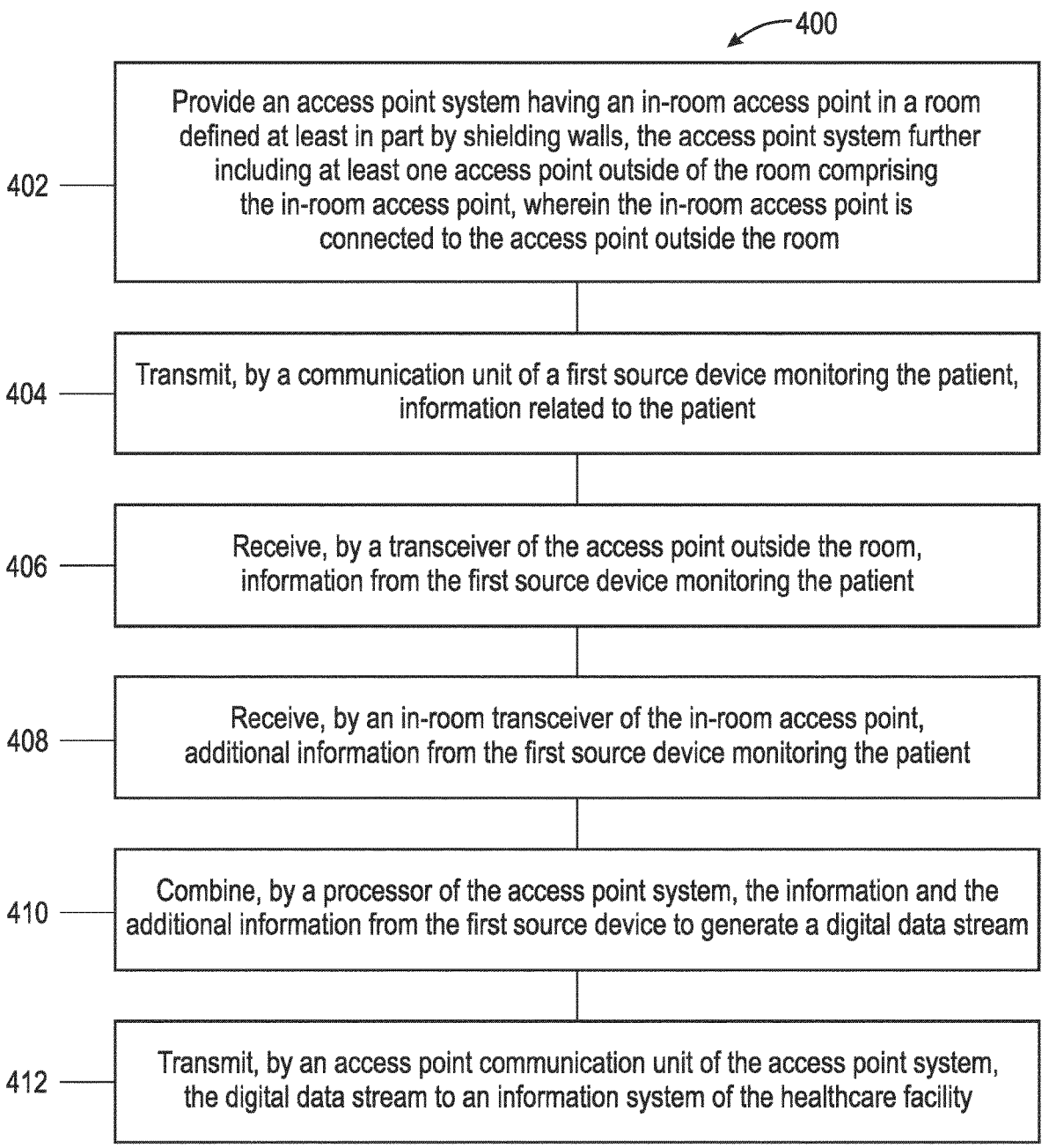

400

402 ——— Provide an access point system having an in-room access point in a room defined at least in part by shielding walls, the access point system further including at least one access point outside of the room comprising the in-room access point, wherein the in-room access point is connected to the access point outside the room 404 ——— Transmit, by a communication unit of a first source device monitoring the patient, information related to the patient 406 ——— Receive, by a transceiver of the access point outside the room, information from the first source device monitoring the patient 408 ——— Receive, by an in-room transceiver of the in-room access point, additional information from the first source device monitoring the patient 410 ——— Combine, by a processor of the access point system, the information and the additional information from the first source device to generate a digital data stream 412 ——— Transmit, by an access point communication unit of the access point system, the digital data stream to an information system of the healthcare facility

Fig. 4

MULTI-TECHNOLOGY WIRELESS COMMUNICATION NETWORK NETWORK FOR MONITORING PATIENT THROUGH-OUT A HEALTHCARE FACILITY

CROSS-REFERENCE TO PRIOR APPLICATIONS

This application is the U.S. National Phase application under 35 U.S.C. § 371 of International Application No. PCT/EP2022/076017, filed on Sep. 20, 2022, which claims the benefit of U.S. Provisional Application No. 63/247,420 filed on Sep. 23, 2021. These applications are hereby incorporated by reference herein.

FIELD OF THE DISCLOSURE

The present disclosure is directed generally to systems and methods for providing continuous wireless connectivity for monitoring patients throughout a healthcare facility including in RF shielded areas, such as, magnetic resonance (MR).

BACKGROUND

Magnetic resonance imaging (MRI) capabilities are increasing and are being applied to more and more patients with acute conditions. These acute care patients are driving the need for evermore comprehensive monitoring for the entire duration these acute care patients are outside the intensive care unit (ICU). Today's hospital networks can manage this increased remote monitoring challenge in most areas throughout the medical facility, however continuous connectivity cannot be guaranteed for patients who require MRI diagnostic imaging to support their care. For example, it is desirable to be able to remotely monitor a sedated patient that is transported to a magnetic resonance (MR) room particularly during the transitions from outside the MR room to inside the MR room and from inside the MR room to outside the MR room.

Currently, hospital networks are configured with break-before-make (BBM) communication protocols to allow a signal path to switch between two different sources. The BBM switching opens or breaks the original signal path before making or closing the new signal path to avoid any momentary shorting between the two signal sources. Unfortunately, BBM communication protocols have the potential to lose data or delay its arrival to a remote nursing station due to retransmissions of the data.

Additionally, the regulatory limits on effective isotropic radiated power (EIRP) are ever-increasing, such as those in the Radio Equipment Directive (RED) in Europe. Some of these new regulations allow more players to use applicable radio systems simultaneously, yet no longer allow one or more players to be louder than the rest. Thus, systems cannot include radios with sufficient power to continuously penetrate the shielded walls of MR rooms. Additionally, current systems which can communicate through a MR room shield are being regulated out of use due to incompatibility with systems located outside the MR exam room.

Thus, there is a need in the art for improved systems and methods for providing continuous wireless connectivity for monitoring patients throughout a healthcare facility including in RF shielded areas, such as, magnetic resonance. There is also a need in the art for improved communication methods and systems that support multiple technologies, thus providing the flexibility for each user to utilize an optimized wireless communication protocol for their particular application.

SUMMARY OF THE DISCLOSURE

The present disclosure is directed generally to inventive methods and systems for providing continuous wireless connectivity for monitoring patients throughout a healthcare facility. Various embodiments and implementations herein are directed to improved systems or methods that utilize multi-technology access points that support multiple different technologies throughout a healthcare facility. The healthcare facility includes a shielded magnet room such as an MR room. At least one of the multi-technology access points or hubs is located inside the shielded magnet room and at least one other multi-technology access point or hub is located outside the shielded magnet room. The multi-technology access points or hubs support a make-before-break (MBB) communication protocol so the patient's information is continuously available to the hospital network, and including a remote central station, e.g., for nurses and other clinical staff. Applicant has recognized and appreciated that access points can be improved upon to provide enhanced wireless capability. Applicant has further recognized and appreciated that such enhanced access points can be used to provide continuous wireless communication between a very low attenuation environment and an environment with high attenuation or shielding, such as, a MR exam room, metal elevators, freezers, etc. The improved systems and methods described herein also support the ever-increasing regulatory limits on effective isotropic radiated power (EIRP).

Generally, in one aspect, a system for providing continuous wireless connectivity for monitoring a patient throughout a healthcare facility is provided. The system includes a first source device comprising a communication unit configured to transmit information related to a patient and an access point system located in the healthcare facility. The access point system includes an in-room access point in a room defined at least in part by shielding walls, the in-room access point comprising an in-room transceiver configured to receive information related to the patient from the first source device. The access point system further includes an access point outside the room and connected to the in-room access point, the access point comprising a transceiver configured to receive additional information related to the patient from the first source device. The access point system further includes a processor configured to communicate with the transceiver and the in-room transceiver to combine the information and the additional information from the first source device to generate a digital data stream. The access point system further includes an access point communication unit configured to transmit the digital data stream to an information system of the healthcare facility.

According to an embodiment, the processor is further configured to maintain a first communication link between the in-room transceiver and the first source device while establishing a second communication link between the transceiver and the first source device.

According to an embodiment, the processor is further configured to maintain a first communication link between the transceiver and the first source device while establishing a second communication link between the in-room transceiver and the first source device.

According to embodiments, the access point is connected to the in-room access point through a router.

According to an embodiment, the first source device, the transceiver, and the in-room transceiver are configured to communicate according to a first technology, and wherein the access point and the in-room access point are configured to communicate according to at least a second technology that is different than the first technology.

According to embodiments, the room is a magnet room and the shielding walls comprise electromagnetic interference shielding material comprising copper or steel.

According to an embodiment, the transceiver or the in-room transceiver is a software-defined radio.

According to an embodiment, the access point communication unit is configured to transmit the digital data stream to a display of the information system of the healthcare facility.

Generally, in another aspect, a method for providing continuous wireless connectivity for monitoring a patient throughout a healthcare facility is provided. The method includes providing an access point communication system in the healthcare facility, the access point communication system comprising an in-room access point in a room defined at least in part by shielding walls, the access point system further comprising an access point outside of the room and connected to the in-room access point. The method further includes transmitting, by a communication unit of a first source device monitoring the patient, information related to the patient; receiving, by a transceiver of the access point outside the room, information from the first source device monitoring the patient; receiving, by an in-room transceiver of the in-room access point, additional information from the first source device monitoring the patient; combining, by a processor of the access point system, the information and the additional information from the first source device to generate a digital data stream, and transmitting, by an access point communication unit of the access point system, the digital data stream to an information system of the healthcare facility.

According to an embodiment, the method further comprises maintaining, by the processor, a first communication link between the in-room transceiver and the first source device while establishing a second communication link between the transceiver and the first source device.

According to an embodiment, the method further comprises maintaining, by the processor, a first communication link between the transceiver and the first source device while establishing a second communication link between the in-room transceiver and the first source device.

According to embodiments, the access point is connected to the in-room access point through a router.

According to an embodiment, the method further comprises communicating among the first source device, the transceiver, and the in-room transceiver according to a first technology, and communicating among the access point and in-room access point according to at least a second technology that is different than the first technology.

According to an embodiment, the transceiver or the in-room transceiver is a software-defined radio.

According to an embodiment, the method further includes transmitting, by the access point communication unit, the digital data stream to a display of the information system of the healthcare facility.

In various implementations, a processor or controller may be associated with one or more storage media (generically referred to herein as "memory," e.g., volatile, and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects as discussed herein. The terms "program" or "computer program" are used herein in a generic sense to refer to any type of computer code (e.g., software or microcode) that can be employed to program one or more processors or controllers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

FIG. 4 is a flowchart of a method for providing continuous wireless connectivity for monitoring patients throughout a healthcare facility using an access point communication system, according to aspects of the present disclosure.

DETAILED DESCRIPTION OF EMBODIMENTS

The present disclosure describes various embodiments of improved systems and methods for providing continuous wireless communication between a very low attenuation environment (e.g., inside a typical building) and an environment with significant attenuation or shielding (e.g., MR exam rooms, metal elevators, freezers, etc.). Applicant has recognized and appreciated that enhanced multi-technology wireless access points can be used to support a make-before-break communication protocol so a patient's information is continuously available to the hospital network and a remote central station. The improved systems and methods include providing an access point communication system in a healthcare facility, the access point communication system including at least one in-room access point in a magnet room defined at least in part by shielding walls. The access point system further includes at least one access point outside of the magnet room, wherein the at least one in-room access point is connected to the at least one access point. The improved systems and methods further include transmitting, by a communication unit of a first source device monitoring the patient, information related to a patient. The improved systems and methods further include receiving, by transceivers of the access points inside and outside the magnet room, information from the first source device monitoring the patient and transmitting the information to an information system of the healthcare facility. The improved systems and methods provide the advantages described herein as well as others as should be appreciated.

Figure 1:
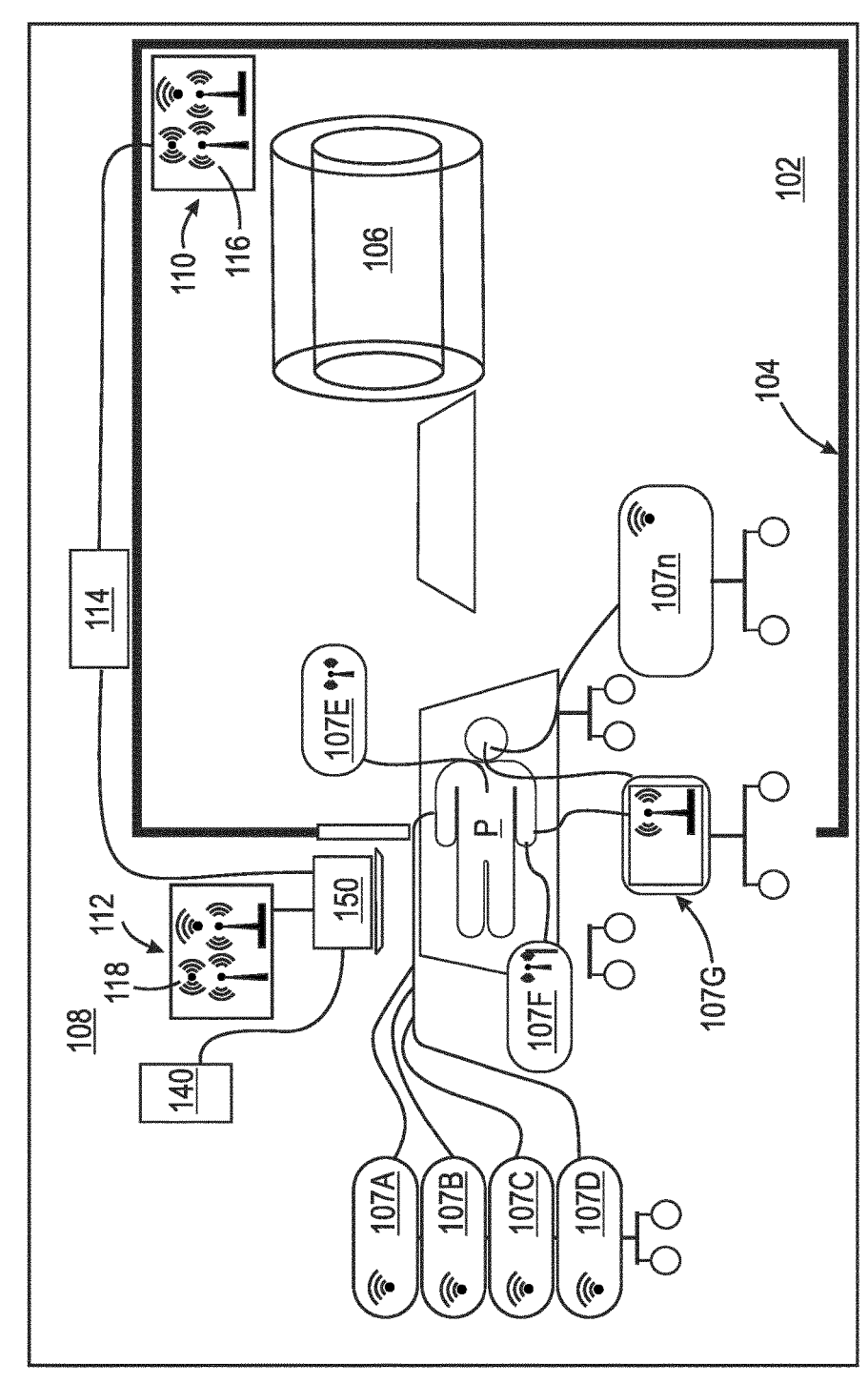
FIG. 1 is a schematic representation of an access point communication system in a healthcare facility, according to aspects of the present disclosure.

Referring to FIG. 1, a schematic representation of an access point communication system 100 in a healthcare facility is provided. The example healthcare facility illustrated in FIG. 1 includes a MRI exam room or magnet room 102 defined at least in part by shielding walls 104. The shielding walls provide RF shielding by enclosing or surrounding the magnet room with steel or copper sheeting, metal foil, plasma, high metallic content (e.g., metal mesh) glass, or other suitable conductive layers such as wire mesh. In embodiments, the shielding walls are made of electromagnetic interference (EMI) shielding material, not limited to cooper or steel. The shielding material can be embedded in the walls or otherwise connected to the walls. The shielding forms a Faraday cage around the room and prevents external signals that are in a spectrum that may interfere with the operation of the scanner 106. The shielding also limits detrimental emissions from the scanner 106. The magnet room 102 includes a scanner 106 configured to image a patient P. In the embodiment depicted in FIG. 1, a variety of medical devices 107A, 107B, 107C, 107D, 107E, 107F, 107G, . . . 107n can be coupled with the patient P to provide monitoring of the patient's physiological parameters, where n is equal to or greater than 1. Although FIG. 1 shows a horizontal bore-type MRI system with the patient P to be loaded into the MRI bore, it should be appreciated that scanner 106 can alternatively be an open MRI, a positron emission tomography (PET) imaging device, a single-positron emission computed tomography imaging device and so on.

The healthcare facility shown in FIG. 1 also includes a control room 108 located outside and adjacent to the magnet room 102. Control room 108 does not include shielding walls 106 as are included in magnet room 102 except for the wall between the control room 108 and the magnet room 102. In an example embodiment depicted in FIG. 1, devices 107A, 107B, 107C, and 107D are intravenous (IV) pumps, device 107E is an electrocardiogramaensor, device 107F is a blood pressure sensor $SpO_2$, device 107G is a patient monitor, and device 107n is a ventilation machine. However, the invention should not be limited to the devices depicted in FIG. 1. The devices coupled with the patient as used herein can include any sensors, pumps, monitors, or devices, including, but not limited to, ECG sensors, IV pumps, blood pressure sensors, heart rate monitors, pulse sensors, thermometers, respiratory sensors, exhaled gas sensors, and so on. It should further be appreciated that the devices need not all be medical devices. Some of the devices can include or embody devices that provide a user experience for the patient, such as, an augmented reality device that can be used to calm a patient. It should also be appreciated that one or more of the devices shown in FIG. 1 can additionally or alternatively be coupled to or integrated within scanner 106. While traditionally many of these devices are attached to the patient with wires, more and more of these devices are capable of communicating data wirelessly via a gateway that connects to a healthcare facility's network and/or transmits data or information to data storage for monitoring, control, or evaluating in real-time or offline after storage. Wireless sensors are also beneficial because they avoid using conductive wires that could otherwise couple with magnetic field gradients and heat up due to induced eddy currents.

The access point system 100 further includes an in-room access point 110 in magnet room 102 and access point 112 in control room 108. Although FIG. 1 shows access point 112 in control room 108, it should be appreciated that access point 112 can be anywhere outside magnet room 102, and preferably close in proximity to the doorway of magnet room 102. The in-room access point 110 is connected to access point 112. In example embodiments, in-room access point 110 is connected to access point 112 by router 114. However, it should be appreciated that in-room access point 110 can be connected to access point 112 by any suitable alternative. The term access point as used herein refers to a network entity that is configured to communicate with source devices and may also commonly be referred to as a base station, node, transmit-receive point (TRP), and so on. Each access point is configured to provide communication coverage for a particular geographic area that depends on the application.

In embodiments, in-room access point 110 includes multiple transceivers 116 that are configured to communicate using different technologies. The different technologies refer to wireless communication technologies, such as, radio-frequency identification (RFID) technology, Wi-Fi technology, Bluetooth technology, technologies used by mobile phone communication systems such as cellular data technologies, and proprietary links, etc. In embodiments, in-room access point 110 includes a single transceiver 116 configured to communicate using at least one wireless technology. Access point 112, that is outside magnet room 102, includes multiple transceivers 118 that are configured to communicate using different technologies, like in-room access point 110. In embodiments, access point 112 includes a single transceiver 118 configured to communicate using at least one wireless technology that is the same as the wireless technology used for in-room access point 110. Thus, if in-room access point 110 includes a transceiver configured to communicate using Bluetooth technology, access point 112 includes a transceiver configured to communicate using Bluetooth technology. If in-room access point 110 includes transceivers configured to communicate using Bluetooth technology, Wi-Fi technology, RFID technology, cellular data technologies, and proprietary links, access point 112 includes transceivers configured to communicate using the same technologies. In embodiments, in-room access point 110 supports additional wireless technologies than access point 112. In other embodiments, access point 112 supports more wireless technologies than in-room access point 110.

The integration of multiple transceivers provides flexibility for each wireless device (e.g., 107A-107n) to use an optimized wireless communication protocol for its particular application in its location whether it's in a magnet room, for example, or otherwise. In embodiments, at least one transceiver 116 and 118 is a software-defined radio. The term software-defined radio as used herein refers to a radio communication system where components that have been traditionally implemented in hardware (e.g., mixers, filters, amplifiers, modulators/demodulators, detectors, etc.) are instead implemented by means of software. Advantageously, software-defined radios allow for additional flexibility in the technologies being utilized. Currently, traditional access points do not offer a variety of wireless communication protocols. The access points of the present disclosure are capable of offering a plurality of wireless communication protocols thereby improving upon traditional access points.

Figure 2A:
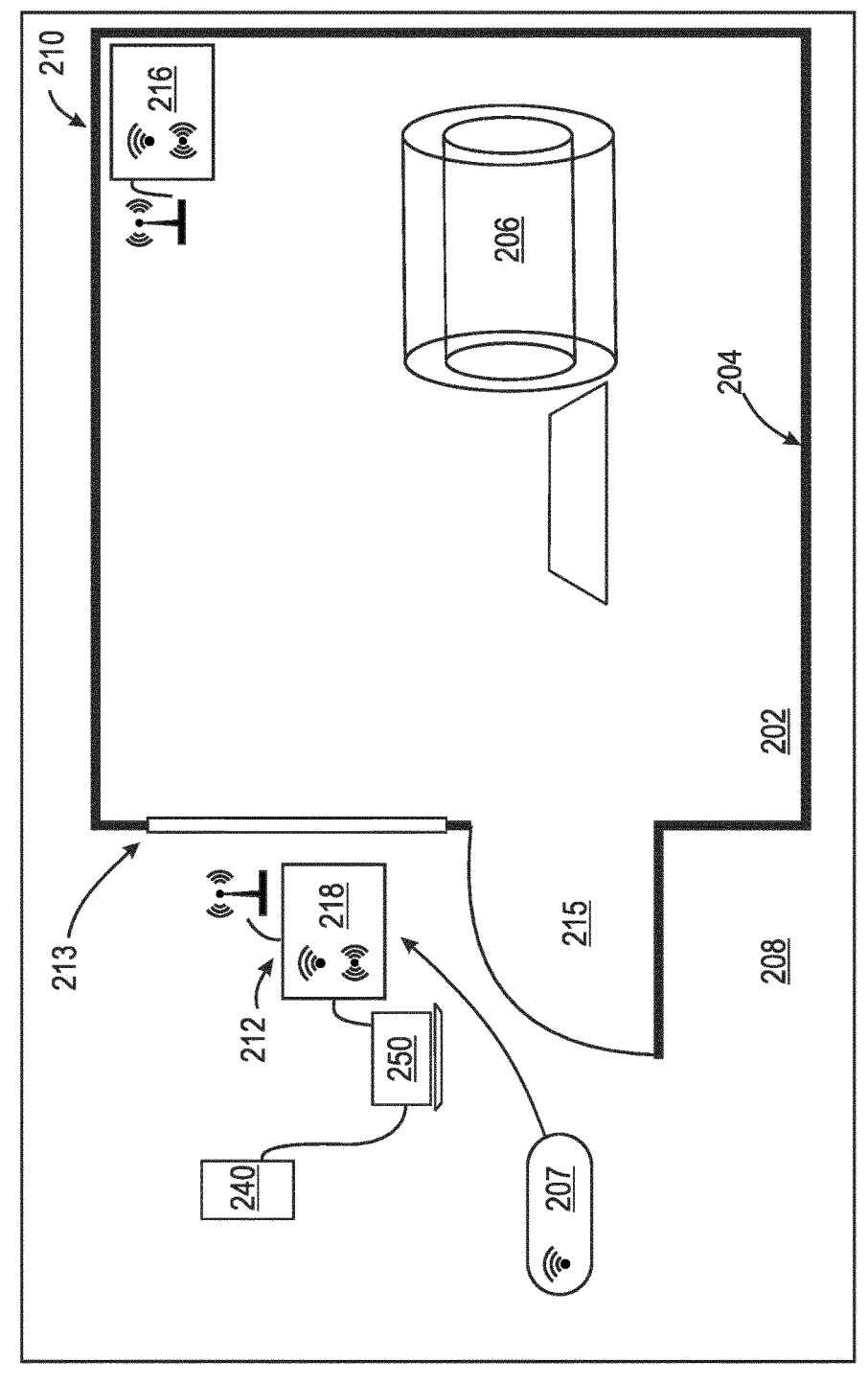
FIGS. 2A, 2B, and 2C are schematic representations of an access point communication system in a healthcare facility, according to aspects of the present disclosure.
Figure 2B:
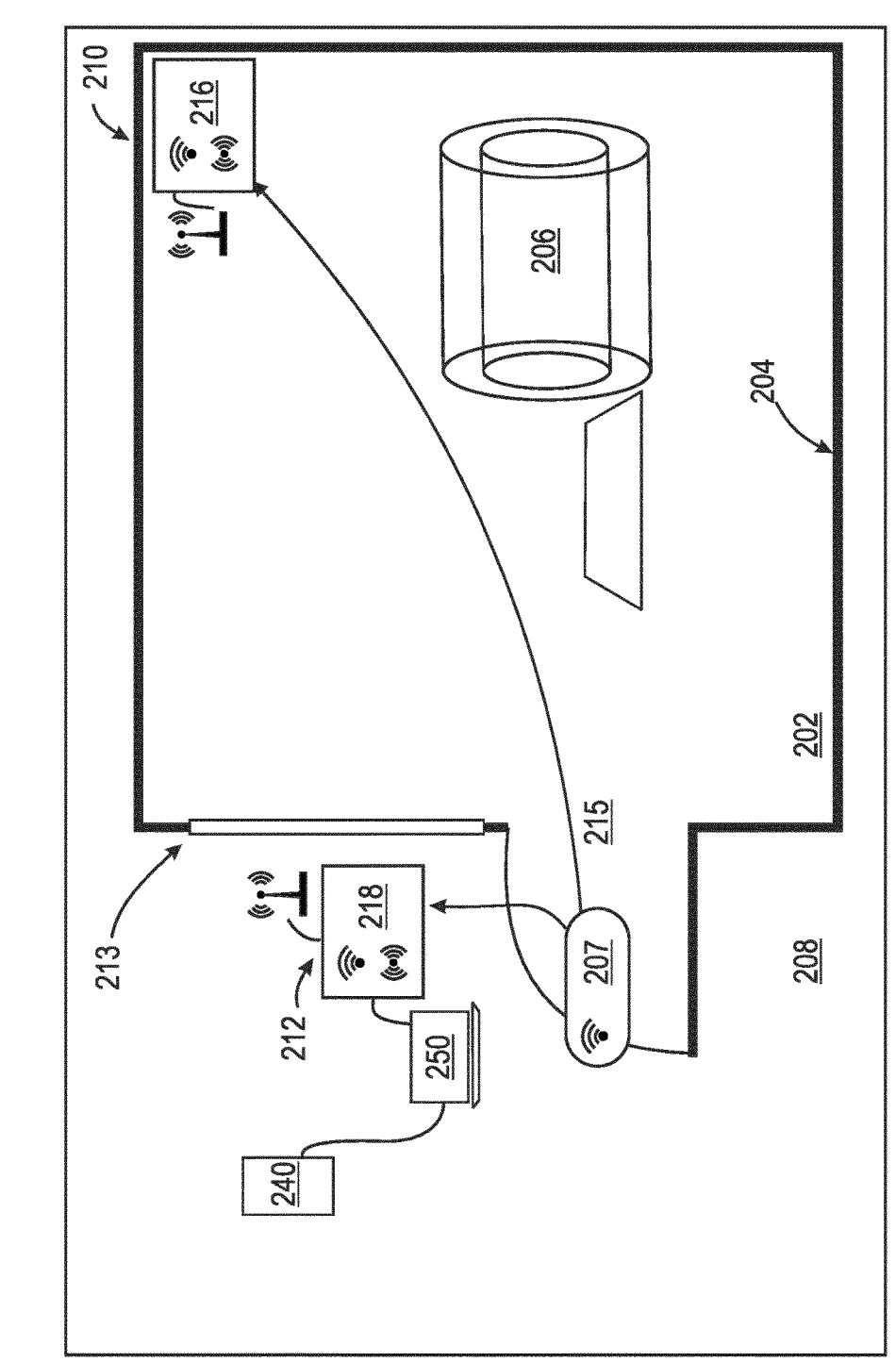
Figure 2C:
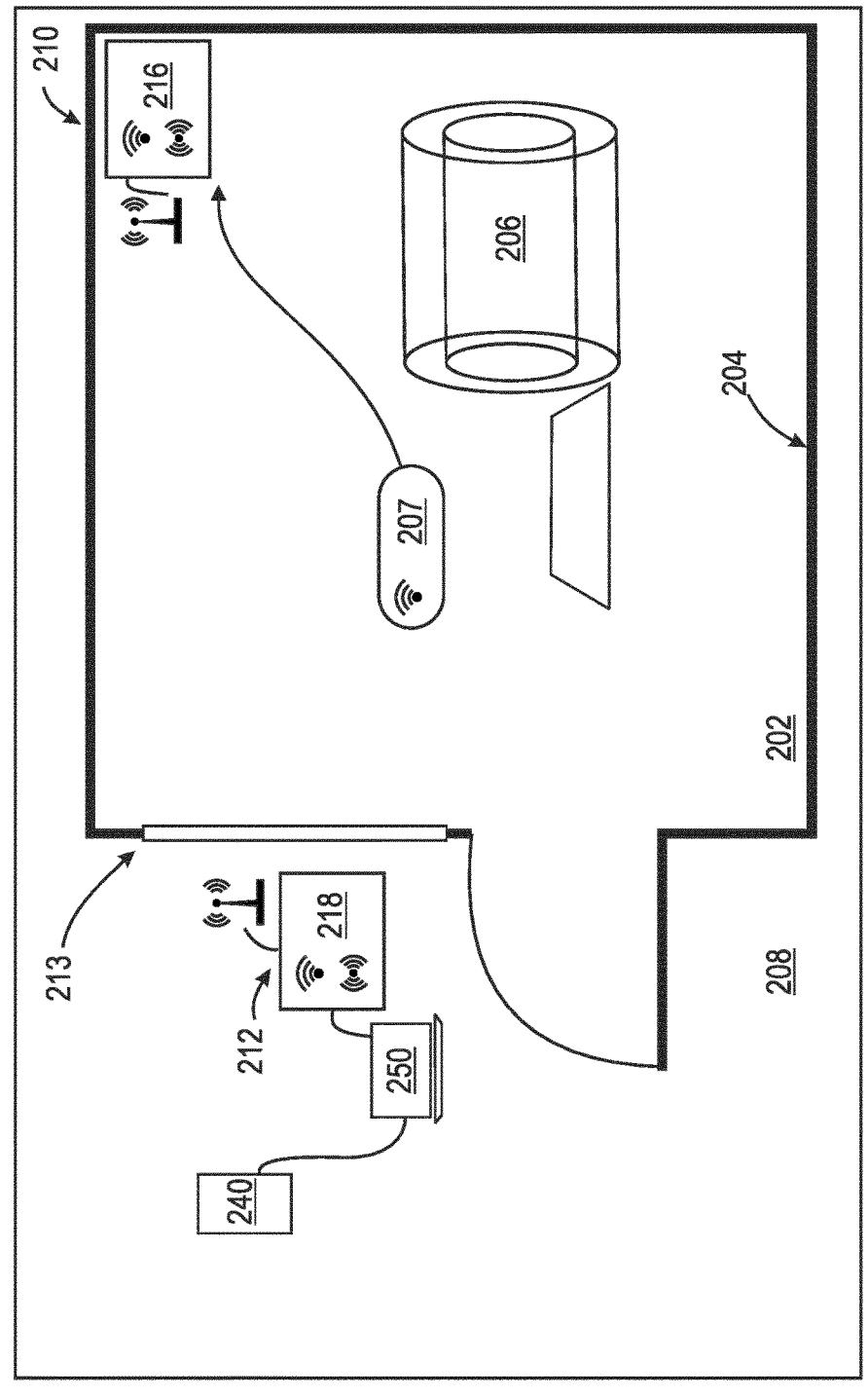

FIGS. 2A, 2B, and 2C show schematic representations of another access point communication system 200 in a health-care facility. The sequence depicted in FIGS. 2A, 2B, and 2C demonstrates an embodiment where a source device 207 associated with a patient is being transported to a MR room. Of course, it should be appreciated that the invention is not limited to the depicted sequence. In other embodiments, the source device 207 can begin in a MR room and thereafter end up in an ICU, for example, after transport. In any of these contemplated embodiments, the access point commu-nication systems described herein facilitate seamless wire-less connections during the transports into and out of the MR room. In embodiments, a single source device 207 can utilize the multiple different technologies of access points 210 and 212 as described herein. As shown in FIGS. 2A, 2B, and 2C, system 200 includes in-room access point 210 in magnet room 202 and access point 212 in control room 208 or otherwise outside of magnet room 202. Access point 212 can be arranged on a first side of window 213 of magnet room 202 and in-room access point 210 can be arranged on a second side of window 213, opposite access point 212. Both access points 210 and 212 can be connected to each other through a cellular network, any other suitable network, or otherwise. In embodiments, in-room access point 210 includes transceivers 216 that are configured to communi-cate using different technologies separately or simultane-ously. Similarly, access point 212 includes transceivers 218 that are configured to communicate using different technolo-gies separately or simultaneously. The transceivers 216 and 218 can communicate with source device 207.

As shown in FIG. 2A, source device 207 can be connected to one or more transceivers 218 of access point 212 before the device 207 is brought within doorway 215 of magnet room 202 or otherwise within communication range of access point 212. As shown in FIG. 2B, when device 207 is within doorway 215 or otherwise in communication range of both access points 210 and 212, device 207 can be in communication with both access points 210 and 212 simul-taneously to support a make-before-break communication protocol as further described below. In embodiments, device 207 can utilize one wireless technology link with access point 212 while utilizing another wireless technology link with access point 210. For example, in embodiments, a scanning procedure which was being conducted by access point 212 can be moved over to access point 210 or vice versa. When device 207 is within magnet room 202, as shown in FIG. 2C, at least one connection has been estab-lished with in-room access point 210 and the one or more connections with access point 212 are broken. Notably, device 207 can utilize any one or more of the different technologies supported by the transceivers 216 of in-room access point 210. In embodiments, device 207 can commu-nicate using a first technology transceiver 216 and then switch to a second technology transceiver 216 when the second technology is more efficient and/or requires less battery power in device 207, for example.

The embodiments described with reference to FIGS. 2A, 2B, and 2C depict some ways to realize the soft hand-off procedure enabled by the system 200. Additionally, the embodiments show how the access points communicate utilizing different technologies with the same source device. This approach allows simultaneous communications with both access points 210 and 212.

Figure 3:
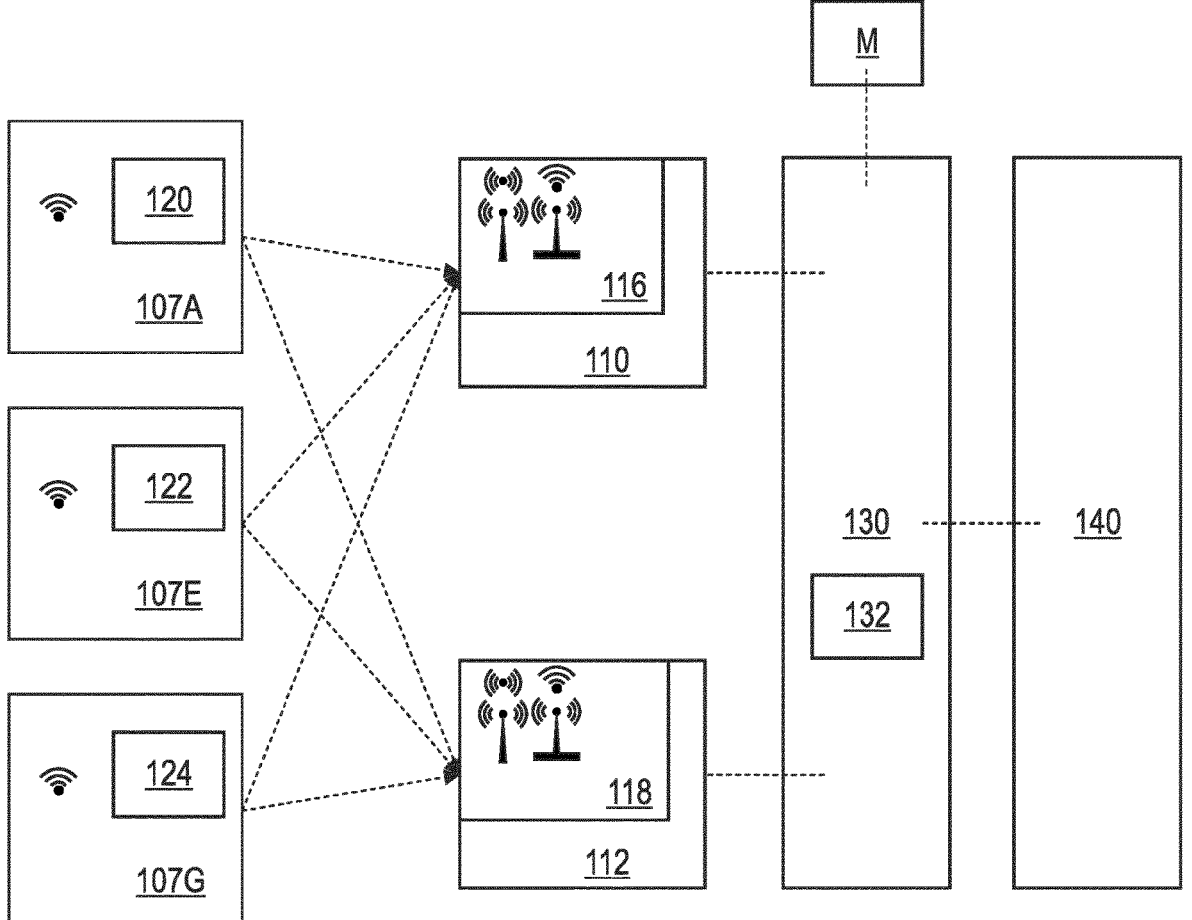
FIG. 3 is a schematic representation of access points of an access point communication system transmitting data from source devices to an information system of a healthcare facility, according to aspects of the present disclosure.

FIG. 3 shows a schematic representation of access points 110 and 112 transmitting data from source devices (e.g., devices 107A, 107E, and 107G) to an information system 140 via one or more processors 130. It should be appreciated that the discussion pertaining to FIG. 3 also applies to the access points 210 and 212 in FIGS. 2A, 2B, and 2C. In embodiments where access points 110 and 112 are config-ured to receive data streams from multiple source devices, access points 110 and 112 can include a multiplexor or other suitable alternative configured to combine the individual data streams into a single data stream. In embodiments, transceivers 116 and 118 of access points 110 and 112 receive information from communication unit 120 of source device 107A only. In embodiments, transceivers 116 and 118 of access points 110 and 112 receive information from communication unit 120 of source device 107A and com-munication unit 122 of source device 107E only. In embodi-ments, transceivers 116 and 118 of access points 110 and 112 receive information from communication unit 120 of source device 107A, communication unit 122 of source device 107E, and communication unit 124 of source device 107G. In additional embodiments, transceivers 116 and 118 of access points 110 and 112 receive information from addi-tional or alternative communication units of additional or alternative source devices.

One or more processors 130 receive data from and provide data to each of transceivers 116 and 118 for com-munication with the information system 140. One or more processors 130 are capable of executing instructions stored in memory M or any suitable storage device or otherwise processing data to, for example, perform the one or more steps of the method described herein. One or more proces-sors 130 may be formed of one or more multiple modules. The memory or storage may include one or more machine-readable storage media such as read-only memory (ROM), random-access memory (RAM), magnetic disk storage media, optical storage media, flash-memory devices, or similar storage media. In various embodiments, the storage may store instructions for execution by the processors 130 or data upon which the processors 130 may operate. For example, an operating system for controlling various opera-tions of system 100 may be stored in memory M. It should be appreciated that various information described as being stored in memory M may be additionally or alternatively stored in a separate memory device. The memory and storage described herein may be considered to be non-transitory machine-readable media. As used herein, the term non-transitory means to exclude transitory signals but to include all forms of storage, including both volatile and non-volatile memories.

The processors 130 may take any suitable form, including but not limited to a microprocessor, microcontroller, mul-tiple microcontrollers, circuitry, field programmable gate array (FPGA), application-specific integrated circuit (ASIC), a single processor, or plural processors. Memory M can take any suitable form, including a non-volatile memory and/or RAM. Memory M may include various memories such as, for example L1, L2, or L3 cache or system memory. As such, the memory M may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of access point communication system 100. It will be apparent that, in embodiments where the processor implements one or more of the functions described herein in hardware, the software described as corresponding to such functionality in other embodiments may be omitted.

While system 100 is generally shown as including one of each described component, the various components may be duplicated in various embodiments. For example, processor 130 may include multiple microprocessors that are configured to independently execute the methods described herein or are configured to perform steps or subroutines of the methods described herein such that the multiple processors cooperate to achieve the functionality described herein. Further, where one or more components of system 100 is implemented in a cloud computing system, the various hardware components may belong to separate physical systems. For example, processor 130 may include a first processor in a first server and a second processor in a second server. Many other variations and configurations are possible.

Access point communication unit 132 may include one or more devices for enabling communication with other hardware devices. For example, communication unit 132 may include a network interface card (NIC) configured to communicate according to the Ethernet protocol. Additionally, communication unit 132 may implement a TCP/IP stack for communication according to the TCP/IP protocols. Various alternative or additional hardware or configurations for communication unit 132 are contemplated.

Additionally, it should be appreciated that one or more processors 130 can be implemented in either or both of access points 110 and 112 in embodiments.

When a patient is being transported from an ICU to a MR room, access point communication system 100 is configured to maintain a connection between the one or more source devices 107A-107n and access point 112 while the one or more source devices 107A-107n are being handed over to the in-room access point 110. To do this, the one or more processors 130 are configured to compare the one or more signals from the one or more source devices 107A-107n received by the access points 110 and 112. If there is no signal received from the in-room access point 110, then the one or more processors 130 maintains the connection between the one or more source devices 107A-107n and access point 112. If a signal is received from the in-room access point 110 by the one or more processors 130, the one or more processors 130 can send a handover request to access point 110. Access point 110 can send a handover response to the one or more processors 130. The handover response can acknowledge the request and/or indicate an ability to complete the handover procedure. After the one or more processors 130 receive the handover response, the one or more processors 130 can initiate the make-before-break procedure. While the source devices 107A-107n continue to exchange information with access point 112, the source devices 107A-107n can establish a connection with access point 110. Once the connection with access point 110 is established, access point 110 can transmit information to the one or more processors 130 to indicate that the connection is complete. While the door to magnet room 102 is open, the signals from the one or more source devices 107A-107n can reach both access points 110 and 112 and data can be transmitted from the source devices 107A-107n to the information system 140. The connection to either or both access points 110 and 112 continues seamlessly as the door to the magnet room 102 shuts. After the door closes and the signal to access point 112 decreases in strength and/or experiences interruptions, the one or more processors 130 can break the connection between the one or more source devices 107A-107n and access point 112. In alternate embodiments, the connection between the one or more source devices 107A-107n and access point 112 can be maintained until the one or more source devices 107A-107n no longer have access to in-room access point 110.

If the connection between the one or more source devices 107A-107n and access point 112 breaks while the patient P is in the magnet room 102, access point communication system 100 can proceed as follows when a patient is being transported from a MR room to an ICU. It should also be appreciated that the following can apply to a scenario where the one or more source devices 107A-107n start out being coupled with the patient P in the magnet room 102 and proceed to move out from the MR room. In such scenarios, access point communication system 100 can be configured to maintain a connection between the one or more source devices 107A-107n and in-room access point 110 while the one or more source devices 107A-107n are handed over to the access point 112 outside the magnet room 102. To do this, the one or more processors 130 can be configured to compare the one or more signals from the one or more source devices 107A-107n received by the access points 110 and 112. If there is no signal received from the access point 112, then the one or more processors 130 maintains the connection between the one or more source devices 107A-107n and in-room access point 110. The one or more processors 130 continuously or intermittently compare the signals from the source devices and received by the access points 110 and 112 in embodiments. In alternate embodiments, either of the access points can be configured to provide a notification to the one or more processors 130 indicating that signals from the source devices have been received and/or detected. Once a signal is received from the access point 112, the one or more processors 130 can send a handover request to access point 112. Access point 112 can send a handover response to the one or more processors 130. The handover response can acknowledge the request and/or indicate an ability to complete the handover procedure. After the one or more processors 130 receive the handover response, the one or more processors 130 can initiate the make-before-break procedure. While the source devices 107A-107n continue to exchange information with in-room access point 110, the source devices 107A-107n establish a connection with access point 112. Once the connection with access point 112 is established, access point 112 can transmit information to the one or more processors 130 to indicate that the connection is complete. While the door to magnet room 102 is open, the signals from the one or more source devices 107A-107n can reach both access points 110 and 112 and data can be transmitted from the source devices 107A-107n to the information system 140. The connection to either or both access points 110 and 112 continues seamlessly. After the patient leaves the magnet room 102 and the signal to access point 110 decreases in strength and/or experiences interruptions, the one or more processors 130 can break the connection between the one or more source devices 107A-107n and in-room access point 110. Prior to, during, and after the handover procedures, the one or more processors 130 are configured to process the data from the one or more source devices to remove any redundancies, etc.

With reference to FIG. 4, a flowchart of a method 400 for providing continuous wireless connectivity for monitoring patients throughout a healthcare facility using an access point communication system is provided. It should be understood that, unless clearly indicated to the contrary, in any methods claimed herein that include more than one step or act, the order of the steps or acts of the method is not necessarily limited to the order in which the steps or acts of the method are recited. The access point communication system may be any access point system described or otherwise envisioned herein (e.g., systems 100 or 200). As discussed in greater detail herein, the access point communication system utilizes a make-before-break communication protocol so that the information from the source devices 107A-107n and/or 207 is continuously available to information system 140 including a remote central station.

At step 402 of the method, the access point communication system is provided within a healthcare facility. Providing the access point communication system includes installing at least one in-room access point (e.g., 110, 210) in a magnet room of the healthcare facility where the magnet room is defined at least in part by shielding walls. Providing the access point communication system further includes installing at least one access point (e.g., 112, 212) outside of the magnet room (e.g., in a control room adjacent to the magnet room) and connecting the access points.

At step 404 of the method, a communication unit (e.g., 120, 122, 124) of a first source device monitoring the patient transmits information related to the patient. Such transmitted information is received by a transceiver of the access point outside the magnet room at step 406 of the method. At step 408 of the method, information transmitted by the communication unit of the first source device is received by an in-room transceiver. Both access points can receive information from a source device when a patient is being transported from an ICU to a MR room or from the MR room to the ICU, for example.

At step 410 of the method, the one or more processors 130 combine the information from the transceivers of the access points to generate a single digital data stream. In embodiments, the one or more processors 130 process the data to remove any redundancies in the data. At step 412, an access point communication unit of the access point communication system (e.g., 132) transmits the digital data stream to an information system 140, 240 of the healthcare facility. In embodiments, the information system 140, 240 retrieves the digital data stream from the access point communication unit of the access point communication system. In embodiments, the digital data stream can be displayed on a display 150, 250 (shown in FIGS. 1, 2A, 2B, and 2C) in any suitable configuration and/or format. The display 150, 250 can be part of a computing system at a central station for nurses and other clinical staff. The displayed information can be further transmitted to a mobile phone, computer, laptop, wearable device, and/or any other device configured to allow the display of information from the information system of the healthcare facility.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A system for providing continuous wireless connectivity for monitoring a patient throughout a healthcare facility, comprising:

a first source device comprising a communication unit configured to transmit information related to the patient; and an access point system located in the healthcare facility, the access point system comprising:

an in-room access point in a room defined at least in part by shielding walls, the in-room access point comprising an in-room transceiver configured to receive first information related to the patient from the first source device; and an outside-the-room access point outside the room and connected to the in-room access point, the outside-the-room access point comprising an outside-the-room transceiver configured to receive second information related to the patient from the first source device; and a processor configured to communicate with the in-room transceiver and the outside-the-room transceiver to combine the first information from the first source device and the second information from the first source device to generate a digital data stream; and an access point communication unit configured to transmit the digital data stream to an information system of the healthcare facility.

2. The system of claim 1, wherein the processor is further configured to maintain a first communication link between the in-room transceiver and the first source device while establishing a second communication link between the outside-the-room transceiver and the first source device.

3. The system of claim 1, wherein the processor is further configured to maintain a first communication link between the outside-the-room transceiver and the first source device while establishing a second communication link between the in-room transceiver and the first source device.

4. The system of claim 1, wherein the access point is connected to the in-room access point through a router.

5. The system of claim 1, wherein the first source device, the outside-the-room transceiver, and the in-room transceiver are configured to communicate according to a first technology, and wherein the outside-the-room access point and the in-room access point are configured to communicate according to at least a second technology that is different than the first technology.

6. The system of claim 1, wherein the room is a magnet room and the shielding walls comprise electromagnetic interference shielding material comprising copper or steel.

7. The system of claim 1, wherein at least one of the outside-the-room transceiver or the in-room transceiver is a software-defined radio.

8. The system of claim 1, wherein the access point communication unit is configured to transmit the digital data stream to a display of the information system of the healthcare facility.

9. A method for providing continuous wireless connectivity for monitoring a patient throughout a healthcare facility, comprising:

providing an access point communication system in the healthcare facility, the access point communication system comprising: (i) an in-room access point in a room defined at least in part by shielding walls, and (ii) an outside-the-room access point outside of the room and connected to the in-room access point;

transmitting, by a communication unit of a first source device monitoring the patient, first information related to the patient and second information related to the patient;

receiving, by an in-room transceiver of the in-room access point, first information from the first source device monitoring the patient;

receiving, by an outside-the-room transceiver of the outside-the-room access point, second information from the first source device monitoring the patient;

combining, by a processor of the access point system, the first information from the first source device and the second information from the first source device to generate a digital data stream; and transmitting, by an access point communication unit of the access point system, the digital data stream to an information system of the healthcare facility.

10. The method of claim 9, further comprising maintaining, by the processor, a first communication link between the in-room transceiver and the first source device while establishing a second communication link between the outside-the-room transceiver and the first source device.

11. The method of claim 9, further comprising maintaining, by the processor, a first communication link between the outside-the-room transceiver and the first source device while establishing a second communication link between the in-room transceiver and the first source device.

12. The method of claim 9, wherein the access point is connected to the in-room access point through a router.

13. The method of claim 9, further comprising communicating among the first source device, the outside-the-room transceiver, and the in-room transceiver according to a first technology, and communicating among the outside-the-room access point and the in-room access point according to at least a second technology that is different than the first technology.

14. The method of claim 9, wherein at least one of the outside-the-room transceiver or the in-room transceiver is a software-defined radio.

15. The method of claim 9, further comprising transmitting, by the access point communication unit, the digital data stream to a display of the information system of the healthcare facility.

* * * * *